United States Patent [19]  
Hoffmann et al.

[11] 4,021,491  
[45] May 3, 1977

[54] MANUFACTURE OF 2,6,6-TRIMETHYL-CYCLOHEX-2-EN-1-ONE

[75] Inventors: Werner Hoffmann, Neuhofen; Manfred Baumann, Mannheim, both of Germany

[73] Assignee: BASF Aktiengesellschaft, Ludwigshafen, Germany

[22] Filed: Jan. 19, 1976

[21] Appl. No.: 650,517

[30] Foreign Application Priority Data

Feb. 6, 1975 Germany .......................... 2504930

[52] U.S. Cl. .................. 260/586 C; 260/345.9; 260/593 R; 260/586 R
[51] Int. Cl.$^2$ ............................... C07C 45/00
[58] Field of Search ........ 260/586 R, 345.9, 586 C, 260/593 R

[56] References Cited

UNITED STATES PATENTS

| | | | |
|---|---|---|---|
| 3,691,205 | 9/1972 | Hoffmann et al. | 260/345.9 |
| 3,812,190 | 5/1974 | Petrovich et al. | 260/586 |
| 3,857,892 | 12/1974 | Wehrli | 260/586 R |
| 3,932,510 | 1/1976 | Muller | 260/586 R |

*Primary Examiner*—Norman Morgenstern
*Attorney, Agent, or Firm*—Johnston, Keil, Thompson & Shurtleff

[57] ABSTRACT

A process for the manufacture of 2,6,6-trimethyl-cyclo-hex-2-en-1-one by reacting 3-alkoxy-4-methyl-3-pentene or 3-alkoxy-4-methyl-2-pentene or a mixture of these compounds with acrolein, and reacting the resulting 2-alkoxy-2-ethyl-3,3-dimethyl-2,3-dihydro-4H-pyran with acids. The product is an intermediate for numerous syntheses of scents. Furthermore, a number of carotenoid syntheses are based on 2,6,6-trimethyl-yl-cyclohex-2-en-1-one or its hydrogenation product, 2,6,6-trimethyl-cyclohexan-1-one.

2 Claims, No Drawings

MANUFACTURE OF 2,6,6-TRIMETHYL-CYCLOHEX-2-EN-1-ONE

The present invention relates to a process for the manufacture of 2,6,6-trimethyl-cyclohex-2-en-1-one by reaction of 3-alkoxy-4-methyl-3-pentene, 3-alkoxy-4-methyl-2-pentene or a mixture of 3-alkoxy-4-methyl-3-pentene and 3-alkoxy-4-methyl-2-pentene with acrolein and reaction of the resulting 2-alkoxy-2-ethyl-3,3-dimethyl-2,3-dihydro-4H-pyran with acids.

2,6,6-Trimethyl-cyclohex-2-en-1-one is a valuable intermediate for numerous syntheses of scents. For example, damascenone, which is in great demand, may be manufactured therefrom by a simple method, comprising reaction with the lithium derivative of methylethynylcarbinol in liquid ammonia, followed by heating with formic acid (cf. S. Isoe et al., Helv. Chim. Acta, 56, Fasc. 5 (1973), No. 148, page 1,514). Furthermore, a number of carotenoid syntheses are based on 2,6,6-trimethyl-cyclohex-2-en-1-one or its hydrogenation product 2,6,6-trimethyl-cyclohexan-1-one. For further details of the synthesis of the ring components in carotenoid syntheses, reference may be made to O. Isler et al, Helv. Chim. Acta 39 (1956), 259 et seq. Hitherto, 2,6,6-trimethyl-cyclohex-2-en-1-one could only be prepared by involved and expensive methods, e.g. by methylation of 2-methylcyclohexanone with $CH_3I/NaNH_2$ or with dimethyl sulfate in anhydrous ether, purification of the resulting 2,6,6-trimethylcyclohexanone via the crystalline semi-carbazone or by fractionation, subsequent bromination with bromine in acetic acid, and dehydrobromination (cf. O. Isler: "Carotenoids", Birkhauser Verlag, Basel and Stuttgart, 1971, pages 331 - 332).

It is an object of the present invention to provide a process by which 2,6,6-trimethyl-cyclohex-2-en-1-one can be manufactured simply and in good yields.

This object is achieved, surprisingly, by a process for the manufacture of 2,6,6-trimethyl-cyclohex-2-en-1-one wherein the tri-substituted enol-ether of the formula I

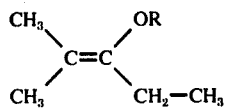

where R is alkyl of 1 to 5 carbon atoms, preferably methyl or ethyl, or the isomeric enol-ether of the formula II

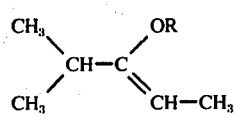

where R has the above meaning, or a mixture of the said isomeric enol-ethers, or a compound which forms a mixture of the said isomeric enol-ethers under the reaction conditions, is reacted with acrolein at from 130° to 220° C, preferably from 150° to 180° C, and the resulting 2-alkoxy-2-ethyl-3,3-dimethyl-2,3-dihydro-4H-pyran of the formula III

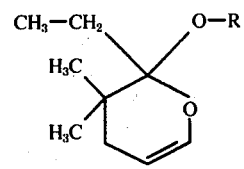

is converted, in the conventional manner, by reaction with acids, to the desired 2,6,6-trimethyl-cyclohex-2-en-1-one of the formula V

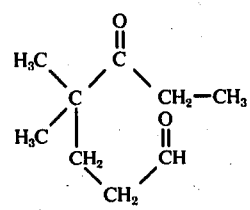

The conversion of 2,3-dihydro-4H-pyran of the formula III to the cyclohexanone of the formula V may be carried out either directly by treatment with strong acids at from 0° to 250° C, preferably from 90° to 140° C, or by first converting the 2,3-dihydro-4H-pyran, by treatment with weak aqueous acids, to the 4,4-dimethyl-heptane-1,5-dione of the formula IV

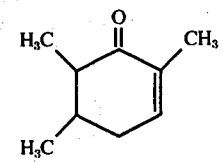

and then converting the latter to the cyclohexenone of the formula V by treatment with strong acids at from 0° to 250° C, preferably from 90° to 140° C.

It is true that Houben-Weyl, Methoden der Organischen Chemie, volume 6/4, pages 355 et seq., discloses that 6-alkoxy-5,6-dihydro-4H-pyrans (or 2-alkoxy-2,3-dihydro-4H-pyrans) can be manufactured by a diene synthesis from a vinyl ether and an α,β-unsaturated aldehyde in accordance with the equation

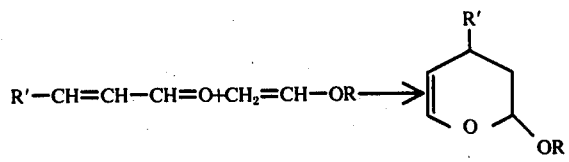

but it has also been disclosed that substituents, e.g. alkyl groups or halogen atoms, on the dienophile component very greatly reduce the tendency of the dienophile to undergo addition reaction with a diene in a diene synthesis (cf. J. G. Martin et al, Chemical Reviews 61, page 540). Accordingly, it was not to be expected that the trialkyl-substituted vinyl ether I could be employed very successfully in a diene synthesis. Nor was it to be expected that a product which is generally an isomer mixture of the vinyl ether of the formula I and the vinyl ether of the formula II can be reacted, with acrolein to give yields of from about 70 to 80% of theory, based on the isomer mixture, of 2-alkoxy-2- ethyl-3,3-dimethyl-2,3-dihydro-4H-pyran, in spite of the fact that according to NMR-spectroscopic data the isomer mixture consists, e.g., of 45% of the isomeric vinyl ether of the formula II in the case of the ethyl ether and even predominantly (95%) of the isomeric vinyl ether of the formula II in the case of the methyl ether, as a result of which at least partial formation of 2-alkoxy-2-isopropyl-3-methyl-2,3-dihydro-4H-pyran was to be expected. In fact, however, no formation of 2-alkoxy-2-isopropyl-3-methyl-2,3-dihydro-4H-pyran has been observed.

The enol-ethers of the formulae I and II required as starting materials may be obtained as isomer mixtures by, e.g. ketalization of ethyl isopropyl ketone with orthoformic acid esters and subsequent acid-catalyzed elimination of alcohol.

The ethyl isopropyl ketone required for this reaction is obtained by reaction of propionic acid and isobutyric acid over suitable ketonizing catalysts at elevated temperatures, with elimination of $CO_2$. Acrolein, stabilized with, e.g., hydoquinone, is a commercially available compound.

Examples of suitable compounds which form a mixture of the isomeric enol-ethers of the formulae I and II under the reaction conditions are ketals of the general formula VI

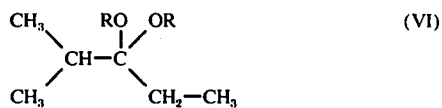

where R has the above meanings, i.e., ketals of ethyl isopropyl ketone.

The reaction of the enol-ethers of the formulae I and II with acrolein may be carried out in the presence of non-polar solvents or without solvents. Examples of non-polar solvents which may be mentioned are ethers, e.g. diethyl ether, tetrahydrofuran and dioxane, aliphatic hydrocarbons, e.g. petroleum ether or gasoline mixtures, cycloaliphatic hydrocarbons, e.g. cyclohexane, aromatic hydrocarbons, e.g. benzene, toluene, xylene, cumene and p-diisopropylbenzene, halogenated hydrocarbons, e.g. chlorobenzene, and mixtures of these solvents. Which of the conventional non-polar solvents is used, has no decisive effect on the reaction, but the more high-boiling solvents are less suitable because they may be difficult to separate off.

The reaction is in general carried out in a closed reaction vessel. The reaction temperature is from 130° to 220° C, and preferably from 150° to 190° C, and the reaction time is in general from 10 to 24 hours.

To prevent polymerization, a small amount of a polymerization inhibitor, e.g. hydroquinone, is generally added to the reaction mixture.

If ketals of ethyl isopropyl ketone are used as starting compounds, it is advantageous to use somewhat higher reaction temperatures than if the enol-ethers themselves are employed. The preferred reaction temperatures when using the ketals are from 160° to 200° C and the reaction time is then from about 10 to 40 hours. In other respects the same reaction conditions are employed as those described for the reaction of the enol-ethers I and II with acrolein.

The ratio of enol-ether of ethyl isopropyl ketone ketal to acrolein may vary from about 2 : 1 to 1 : 2, a ratio of from 1 : 1 to 1 : 1.5 being preferred. If equimolar amounts of acrolein are used, the yield is from 70 to 80%, based on the enol-ether mixture. The reaction mixture may be worked up by distillation under reduced pressure. However, it is not absolutely essential to isolate, in a pure form, the 2-alkoxy-2-ethyl-3,3-dimethyl-2,3-dihydro-4H-pyran obtained; instead, the reaction mixture obtained from the first reaction step may be subjected to the further treatment with acids.

For the direct conversion of the resulting 2-alkoxy-2-ethyl-3,3-dimethyl-2,3-dihydro-4H-pyrans to the desired 2,6,6-trimethylcyclohex-2-en-1-one, strong acids of dissociation constant at least $10^{-3}$ are employed as a rule. Mineral acids, e.g. sulfuric acid, phosphoric acid, hydrogen chloride and hydrogen bromide are preferred. However, strong organic acids, in general those which have a dissociation constant at least equal to the above value, may also be used, e.g. sulfonic acids such as p-toluenesulfonic acid, and also oxalic acid.

In general, the strong acids are used as aqueous solutions. The concentration of the strong aqueous acids is advantageously not less than 0.1 N. The upper limit of concentration can vary within a broad range. Advantageously, the strong aqueous acids used are from 0.1 to about 15 normal, especially from 1 to about 5 normal. The weight ratio of starting material to strong aqueous acid is in general from 5 : 1 to 1 : 10 and preferably from 2 : 1 to 1 : 5. However, it is also possible to use the acids employed according to the invention, especially the hydrogen halides, such as hydrogen chloride and hydrogen bromide, in a substantially anhydrous form, in which case, in general, from 0.1 to 50 per cent by weight, based on starting material, of the anhydrous acid is employed.

The reaction is carried out at from 0° to 250° C, preferably from 90° to 140° C, and, in general, under atmospheric pressure. However, it is also possible to work under superatmospheric pressure, e.g. up to 10 atmospheres, or reduced pressure, e.g. 600 mm Hg. Depending on the reaction temperature and the concentration of the strong aqueous acids, the reaction in general requires from 0.01 to 24 hours.

If aqueous acids are used, the reaction is as a rule carried out without inert organic solvents. However, it is also possible to use inert organic solvents additionally to the aqueous acid, in which case water-soluble inert organic solvents are preferred.

Examples of suitable organic solvents are lower aliphatic carboxylic acids, lower aliphatic alcohols, cyclic ethers and lower aliphatic sulfoxides. More specific examples are acetic acid, propionic acid, chloroacetic acid, methanol, ethanol, isopropanol, isobutanol, tetrahydrofuran, dioxane and dimethylsulfoxide. The weight ratio of strong aqueous acid to inert organic solvent is in general from 5 : 1 to 1 : 5.

The reaction using substantially anhydrous acids is advantageously carried out in an inert organic solvent, and in addition to the solvents already mentioned, aromatic, optionally halogenated, hydrocarbons, e.g. benzene, toluene, xylene and chlorobenzene, or lower aliphatic ethers, e.g. diethyl ether, are preferred.

A method which has proved particularly advantageous is to boil briefly a mixture of the pyran of the formula III with about twice its amount by weight of sulfuric acid, or phosphoric acid, of about 50% strength.

Steam distillation in the presence of strong acids also gives good results.

In general, the reaction mixture is worked up by distillation.

Preferred weak aqueous acids for converting the 2,3-dihydro-4H-pyran of the formula III into the 1,5-dicarbonyl compound of the formula IV are those having a dissociation constant of at most $10^{-3}$. Examples of suitable weak acids are lower aliphatic carboxylic acids, e.g. propionic acid, and especially formic acid or acetic acid. In general, the concentration and amount of the weak aqueous acid used is such, in relation to the 6-alkoxy-5,6-dihydro-4H-pyran used, that the molar ratio of pyran to water is from 1 : 1 to 1 : 50, preferably from 1 : 2 to 1 : 5, and the amount of the acid is from 0.1 mole% to 2,000 mole%, preferably between one hundred mole% and three hundred mole%, based on the pyran.

The conditions for converting 4,4-dimethyl-heptane-1,5-dione into 2,6,6-trimethyl-cyclohex-2-en-1-one are the same as those given above for the direct conversion of the 2,3-dihydro-4H-pyrans of the formula III to 2,6,6-trimethyl-cyclohex-2-en-1-one.

Using the process according to the invention it proves possible to manufacture 2,6,6-trimethyl-cyclohex-2-en-1-one required as a valuable intermediate for the manufacture of numerous scents, in a simple and economical manner even on an industrial scale.

EXAMPLE 1 a. Preparation of 2-ethoxy-2-ethyl-3,3-dimethyl-2,3-dihydro-4H-pyran.

105 g of a mixture of 3-ethoxy-4-methyl-3-pentene (I, with R = $C_2H_5$) and 3-ethoxy-4-methyl-2-pentene (II, with R = $C_2H_5$), which according to the nuclear resonance spectrum comprises 55% of I and 45% of II, 55 g of acrolein and 1 g of hydroquinone are heated at 160° C for 20 hours in a closed reaction vessel.

On working up the reaction mixture by distillation, 105 g of the desired 2-ethoxy-2-ethyl-3,3-dimethyl-2,3-dihydro-4-H-pyran of boiling point 80° - 82° C/18 mm Hg are obtained. This corresponds to a yield of 70% of theory, based on the enol-ether mixture.

b. Preparation of 2,6,6-trimethyl-cyclohex-2-en-1-one.

A mixture of 200 ml of a 50% strength sulfuric acid and 105 g of the 2-ethoxy-2-ethyl-3,3-dimethyl-2,3-dihydro-4H-pyran obtained according to a) is heated to 100° C and steam is then blown into the mixture.

In the course of about 15 minutes, the 2,6,6-trimethylcyclohex-2-en-1-one formed distals off together with the water which distils. The organic phase of the distillate is then separated from the aqueous phase, and dried. Distillation gives 67 g of a product of boiling point 76° - 78° C/16 mm Hg, which according to gas chromatography is practically pure. This corresponds to a yield of 84.5% of theory, based on the pyran starting material.

EXAMPLE 2 a. Preparation of 2-methoxy-2-ethyl-3,3-dimethyl-2,3-dihydro-4H-pyran.

54 g of a mixture of 3-methoxy-4-methyl-3-pentene (I, with R = $CH_3$) and 3-methoxy-4-methyl-2-pentene (II, with R = $CH_3$), which according to the nuclear resonance spectrum comprises about 95% of I and about 5% of II, 32 g of acrolein and 1 g of hydroquinone are heated at 165° C for 20 hours. Distillation of the reaction mixture gives 58 g of the desired 2-methoxy-2-ethyl-3,3-dimethyl-2,3-dihydro-4H-pyran of boiling point 64° - 67° C/13 mm Hg. This corresponds to a yield of 72% of theory.

b. Preparation of 4,4-dimethyl-heptane-1,5-dione 55 g of the dihydro-4H-pyran obtained according to a), 60 g of glacial acetic acid and 30 g of water are stirred for 60 minutes at 50° C. The reaction mixture is distilled in vacuo. 46 g of 4,4-dimethyl-heptane-1,5-dione of boiling point 105° - 110° C/15 mm Hg are obtained. This corresponds to a yield of 91% of theory.

c. Preparation of 2,6,6-trimethyl-cyclohex-2-en-1-one 46 g of the dicarbonyl compound obtained according to b) are added dropwise in the course of 45 minutes, at 130° C, for 100 ml of an 85% strength aqueous phosphoric acid and the reaction mixture is kept at 130° C for a further 15 minutes.

After cooling, the mixture is diluted with twice its volume of water. The aqueous phase is extracted three times with 100 ml of hexane and the extract is washed neutral and dried. Vacuum distillation gives 30 g of 2,6,6-trimethyl-cyclohex-2-en-1-one of boiling point 76° - 78° C/16 mm Hg. This corresponds to a yield of 74% of theory, based on the dicarbonyl compound employed.

EXAMPLE 3

56 g of the diethyl-ketal of ethyl isopropyl ketone, 20 g of acrolein and 0.5 g of hydroquinone are heated at 180° C for 24 hours.

Vacuum distillation of the brown reaction mixture gives 25 g of 2-ethoxy-2-ethyl-3,3-dimethyl-2,3-dihydro-4H-pyran. This corresponds to a yield of 42.5% of theory.

EXAMPLE 4

49 g of the dimethyl-ketal of ethyl isopropyl ketone, 40 g of acrolein and 0.5 g of hydroquinone are heated at 170° for 24 hours. Vacuum distillation of the reaction mixture gives 24 g of a mixture of 2-methoxy-2-ethyl-3,3-dimethyl-2,3-dihydro-4H-pyran and 4,4-dimethyl-heptane-1,5-dione. Accordingly, the dihydro-4H-pyran has already been partially decomposed to the 1,5-dicarbonyl compound.

We claim:

1. A process for the manufacture of 2,6,6-trimethyl-cyclohex-2-en-1-one, wherein the trisubstituted enol-ether of the formula I

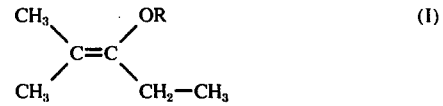

where R is alkyl of 1 to 5 carbon atoms, or the isomeric enol-ether of the formula II

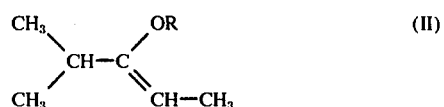

where R has the above meaning, or a mixture of the said enol-ethers, or a compound which forms a mixture of the said enol-ethers under the reaction conditions selected from the group consisting of ketals of the formula VI

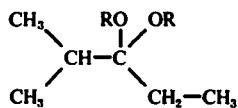
(VI)

is reacted with acrolein at from 130° to 220° C, and the resulting 2-alkoxy-2-ethyl-3,3-dimethyl-2,3-dihydro-4H-pyran of the formula III

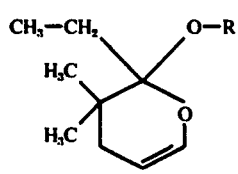
(III)

is converted to 2,6,6-trimethyl-cyclohex-2-en-1-one of the formula V

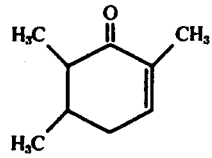
(V)

either directly by treatment with a strong acid having a dissociation constant of at least $10^{-3}$ at from 0° to 250° C or indirectly by a first treatment with a weak aqueous acid having a dissociation constant of at most $10^{-3}$ which yields the 4,4-dimethylheptane-1,5-dione of the formula IV

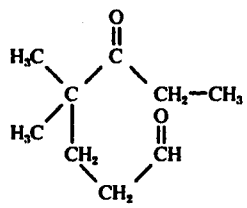
(IV)

followed by treatment with a strong acid having a dissociation constant of at least $10^{-3}$ at from 0° to 250° C.

2. A process as set forth in claim 1, wherein the ketal of the formula VI is reacted with acrolein at from 160° to 200° C.

* * * * *